United States Patent [19]

Masaki

[11] Patent Number: 4,841,972

[45] Date of Patent: Jun. 27, 1989

[54] LOW-FREQUENCY TREATMENT DEVICE DIRECTED TO USE IN BATH

[75] Inventor: Kazumi Masaki, Osaka, Japan

[73] Assignee: Ken Hayashibara, Okayama, Japan

[21] Appl. No.: 116,330

[22] Filed: Nov. 3, 1987

[30] Foreign Application Priority Data

Nov. 11, 1986 [JP] Japan .................................. 61-26830

[51] Int. Cl.$^4$ .......................... A61N 1/00; H05G 00/00
[52] U.S. Cl. ..................................... 128/421; 128/365
[58] Field of Search .................... 128/421, 422, 419 F, 128/24.1, 365

[56] References Cited

U.S. PATENT DOCUMENTS

| | | | |
|---|---|---|---|
| 3,902,502 | 9/1975 | Liss et al. ............................ | 128/422 |
| 4,019,519 | 4/1977 | Geeuling ............................. | 128/422 |
| 4,177,819 | 12/1979 | Kofsky et al. ...................... | 128/422 |
| 4,249,537 | 2/1981 | Lee et al. ............................ | 128/422 |
| 4,586,509 | 5/1986 | Liss et al. ............................ | 128/422 |
| 4,665,920 | 5/1987 | Campbell ............................ | 128/422 |

FOREIGN PATENT DOCUMENTS 1390732 4/1975 United Kingdom .

Primary Examiner—Francis Jaworski
Assistant Examiner—George Manuel
Attorney, Agent, or Firm—Browdy and Neimark

[57] ABSTRACT

A low-frequency treatment device directed to use in bath, comprising a pair of electrodes; a switching transistor; a battery connected in series with the pair of electrodes and a main current path of said switching transistor; and means for oscillating a surged treatment wave at a prescribed time interval, the output terminal being connected with the base of said switching transistor to control its conduction.

5 Claims, 2 Drawing Sheets

LOW-FREQUENCY TREATMENT DEVICE DIRECTED TO USE IN BATH

BACKGROUND OF THE INVENTION

1. Field of the Invention

The present invention relates to a low-frequency treatment device to use in bath as in bath tub.

2. Description of the Prior Art

It is known that electric massage using low-frequency voltage accelerates the growth and regeneration of hair in the subject's skin such as the scalp, as well as promoting its metabolism. Since such electric massage requires a relative high voltage, a commercialized ac source is usually used.

Low-frequency treatment devices using commercialized ac source are not necessarily adequate because they may cause pain and/or burn when used in bath, specifically, in bath tub, for a simultaneous thermotherapy.

For these reasons, batteries are employed to power low-frequency treatment device when it is used in a bath. Conventional device has the drawbacks that it renders attainment of the desired efficacy very difficult because batteries usually provide a relatively low voltage; and that it requires an expensive voltage increasing means such as converter in case a relatively high voltage must be taken out from a battery.

Combination of low-frequency treatment with thermotherapy involves the problem that load resistance variation such as that with the distance between the electrodes or the conditions of the subject's skin renders application of a constant voltage to the subject's skin very difficult.

SUMMARY OF THE INVENTION

The present inventor investigated various means which overcome these drawbacks of conventional device. As the result, the present inventor found that even in case a battery is used a stabilized voltage can be applied to the subject's skin by connecting a battery in series with a main current path of a switching transistor and a pair of electrodes which come into contact with the subject's skin when in use; and controlling the conduction of the switching transistor with an oscillating means that generates a surged treatment wave of an interrupted train of pulses at a prescribed time interval.

More particularly, the present invention relates to a a low-frequency treatment device directed to use in bath, characterized in that it comprises a pair of electrodes; a switching transistor; a battery connected in series with the pair of electrodes and a main current path of said switching transistor; and means for oscillating a surged treatment wave of an interrupted train of pulses at a prescribed time interval, said oscillating means being used to control the conduction of said switching transistor.

Figure 1:
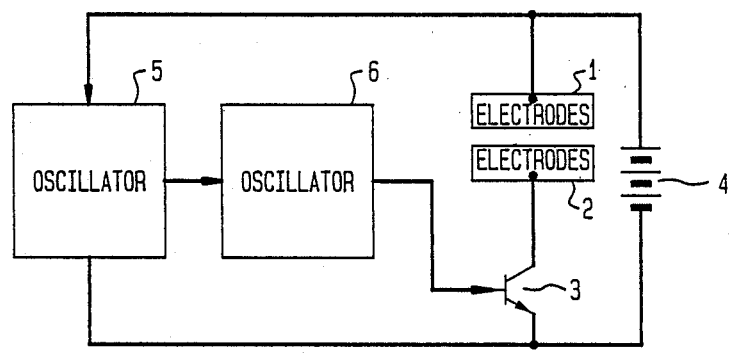
FIG.1 is a block diagram of an embodiment according to the invention.

Throughout the drawings, reference numerals 1 and 2 designate electrodes; 3, switching transistor; 4, battery; 5 and 6, oscillators; T, transistor; R, resistor; and C, capacitor.

DESCRIPTION OF THE PREFERRED EMBODIMENTS

The present invention will hereinafter be explained with reference to the accompanying drawings.

Figure 2:
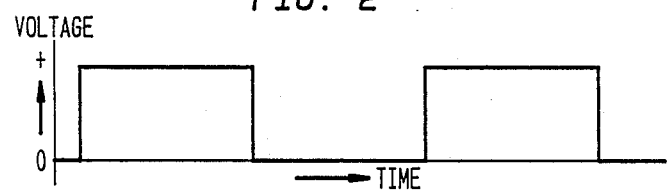
FIGS. 2-4 show the waveform in the embodiment.
Figure 3:
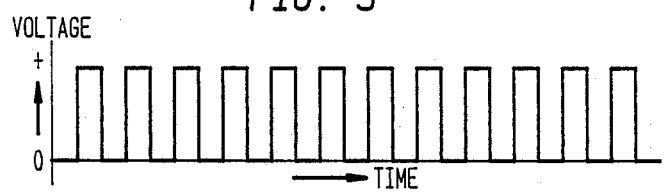

FIG. 1 is the block diagram of an embodiment according to the invention, wherein electrode pair (1) and (2) and a main current path of switching transistor (3) are connected in series with battery (4). The output terminal of oscillator (5) generating a low-frequency square wave as shown in FIG. 2 is connected with the input terminal of another oscillator (6) that generates a treatment wave with a relatively high frequency as shown in FIG. 3. The output terminal of oscillator (6) is connected with the base of switching transistor (3).

Figure 4:
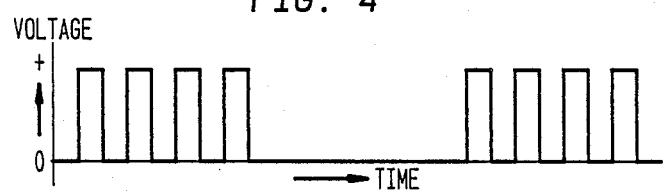

The operation of this embodiment is now explained. Since oscillator (6) is arranged is such manner that it generates a treatment voltage only when oscillator (5) provides a non-zero output voltage, switching transistor (3) becomes conductive at a time interval in accordance with the waveform as shown in FIG. 4. Thus, the subject's body in contact with electrode pair (1) and (2) is interruptedly energized with a surged treatment wave as shown in FIG. 4.

Figure 5:
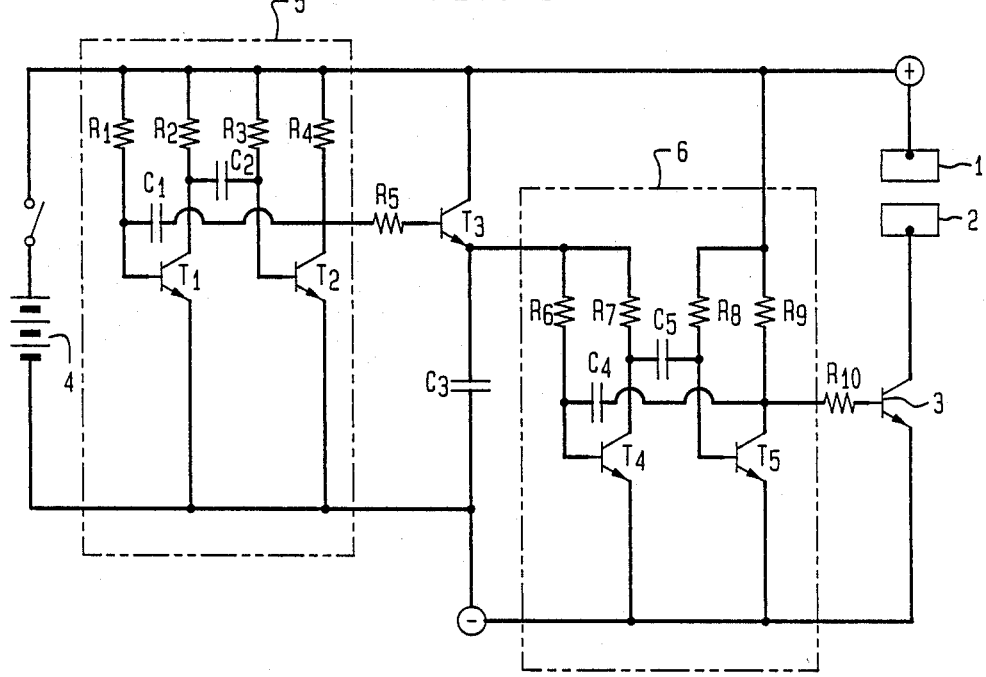
FIG. 5 is the circuit of another embodiment according to the invention.

FIG. 5 is the circuit of another embodiment according to the invention, wherein a multivibrator as oscillator (5) comprising transistors $T_1$ and $T_2$ is used to generate a square wave of a frequency of about 0.1–10 Hz, desirably, 0.5–5 Hz. The output of multivibrator (5) is supplied to another multivibrator generating a square wave with a pulse width of 1/500–1/10 seconds and pulse interval of 1/100–1/5 seconds through an emitter follower that comprises resistor $R_5$ and transistor $T_4$. The latter multivibrator corresponding to oscillator (5) in FIG. 1 is actuated to make switching transistor (3), connected with the output terminal of transistor $T_5$, conductive only when multivibrator (5) provides a non-zero output voltage. Thus, the subject's body in contact with the pair of electrodes (1) and (2) is energized with a surged treatment wave in an interrupted manner as shown in FIG. 4.

Since the internal resistance of switching transistor (3) is lowered to below 10 ohms by supplying an excessive positive current to the base of switching transistor (3) to effect saturation and is several percents of the equivalent resistance of the subject's skin on the electrode pair even when it is assumed that the equivalent resistance is 1,000 ohms, the voltage across the subject's skin can be kept to an approximately prescribed level even when the equivalent resistance varies during one or repeated treatments.

Figure 6:
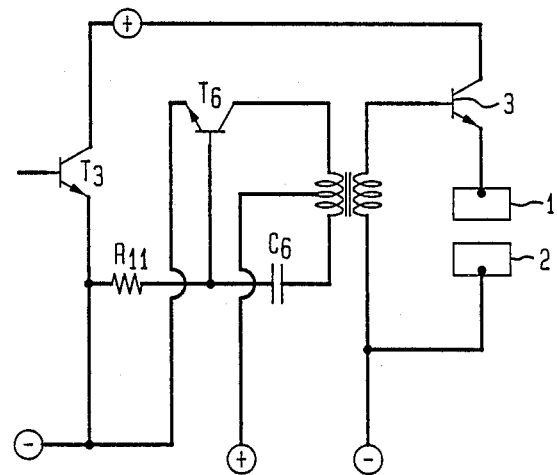
FIG. 6 is the circuit in part of still another embodiment according to the invention.

Oscillator (6) in the embodiment as shown in FIG. 1 may be a blocking oscillator as shown in FIG. 6 that oscillates a diphasic action potential wave. In this case, the subject's skin interruptedly receives a surged diphasic action potential wave.

As described above, since in the invention the switching transistor having a main current path controlled by the electrode pair and low-frequency oscillator is connected in series directly with the battery, a higher voltage utilization factor can be attained.

Furthermore, since in the invention the pair of electrodes and the switching transistor having a main current path controlled by the low-frequency oscillator are connected in series directly with the battery, a sufficient treatment voltage can be applied to the subject's skin without causing electric shock even when used in bath tub.

Additionally, since in the invention the internal resistance of the switching transistor can be extremely lowered with respect to the equivalent resistance of the subject's skin that is in contact with the pair of electrodes, the subject's skin receives a constant treatment voltage.

In addition, since in the present invention the treatment wave interruptedly applied to the subject's skin is surged in a low-frequency voltage, it can cause an appropriate relaxation.

In addition, since the treatment device according to the invention can be used safely even in a bath tub, the affected site such as that in the scalp can be efficiently massaged.

While I have shown and described certain preferred embodiments of the invention it is to be distinctly understood that the invention is not limited thereto but may be otherwise variously embodied within the scope of the following claims.

I claim:

1. A low frequency treatment device for treatment of a subject's body in a bath comprising
   a battery;
   a pair of electrodes which come into contact with the subject's body when in use;
   a switching transistor having a main current path connected with said battery only through said pair of electrodes;
   and means for oscillating an interrupted train of pulses, said oscillating means having an output terminal connected with a base of said switching transistor to control the conduction of the main current path.

2. The low frequency treatment device of claim 1 wherein
   said oscillating means includes
   a first oscillator generating a low-frequency voltage,
   and a second oscillator generating a voltage higher in frequency than that generated by said first oscillator,
   said second oscillator having an input terminal connected with an output terminal of said first oscillator,
   and said second oscillator having the output terminal connected with the base of said switching transistor.

3. The low frequency treatment device of claim 2 wherein
   said first oscillator is a multivibrator and said second oscillator is also a multivibrator.

4. The low frequency treatment device of claim 2 wherein
   said first oscillator is a multivibrator and said second oscillator is a blocking oscillator.

5. A low frequency treatment device comprising
   a bath in which a subject's body is partially immersed;
   a battery;
   a pair of electrodes which come into contact with the subject's body when in use;
   a switching transistor having a main current path connected with said battery only through said pair of electrodes;
   and means for oscillating an interrupted train of pulses at a prescribed time interval, said oscillating means having an output terminal connected with a base of said switching transistor to control the conduction of the main current path.

* * * * *